United States Patent [19]

Ashwell

[11] Patent Number: 5,637,701
[45] Date of Patent: Jun. 10, 1997

[54] PROCESS FOR PREPARING OPTICALLY ACTIVE AMIDE DERIVATIVES

[75] Inventor: Mark A. Ashwell, Slough, United Kingdom

[73] Assignee: John Wyeth & Brother, Limited, Maidenhead, England

[21] Appl. No.: 411,601
[22] PCT Filed: Oct. 8, 1993
[86] PCT No.: PCT/GB93/02090
§ 371 Date: Apr. 11, 1995
§ 102(e) Date: Apr. 11, 1995
[87] PCT Pub. No.: WO94/08983
PCT Pub. Date: Apr. 28, 1994

[30] Foreign Application Priority Data

Oct. 17, 1992 [GB] United Kingdom .............. 9221931

[51] Int. Cl.$^6$ .............. C07D 223/04; C07D 403/06
[52] U.S. Cl. .............. 540/597; 540/598; 540/607; 544/335; 544/336; 544/359; 544/393; 546/195; 546/207; 546/226; 546/233; 546/336; 560/41; 560/44; 564/169
[58] Field of Search .............. 540/597, 598, 540/607; 544/359, 393, 335, 336; 546/195, 207, 233, 226, 336; 560/41, 44; 564/169

[56] References Cited

U.S. PATENT DOCUMENTS

| | | | |
|---|---|---|---|
| 2,776,282 | 1/1957 | Cusic | 544/169 |
| 4,921,958 | 5/1990 | Abou-Gharbia | 544/295 |
| 4,988,814 | 1/1991 | Abou-Gharbia | 544/295 |

FOREIGN PATENT DOCUMENTS

| | | | |
|---|---|---|---|
| 0395312 | 10/1990 | European Pat. Off. | C07D 295/14 |
| 0481744 | 4/1992 | European Pat. Off. | C07D 295/18 |
| 158537 | 9/1992 | Poland . | |
| 2230780 | 10/1990 | United Kingdom | C07D 295/10 |
| 2230781 | 10/1990 | United Kingdom | C07D 295/10 |

OTHER PUBLICATIONS

Rokach et al J. Organic Chemistry, 31 (12), (1966), pp. 4210–4215.
Jonczyk et al, Chemical Abstract 119:249841 for Polish Patent PL 158,537 (Sep. 30, 1992).

*Primary Examiner*—Philip I. Datlow
*Attorney, Agent, or Firm*—Arthur G. Seifert

[57] ABSTRACT

A novel asymmetric synthesis is provided for preparing optically active amides of formula (A) and their salts.

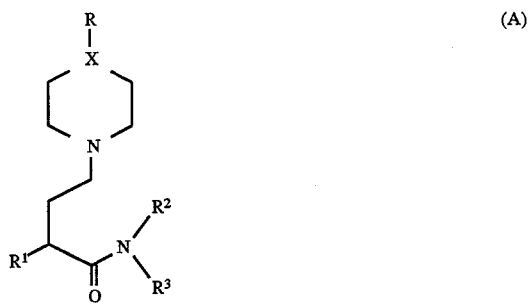

In the formula, X represent —N— or —CH—, R represents a mono or bicyclic aryl or heteroaryl group, $R^1$ is an aryl or heteroaryl radical, and $R^2$ and $R^3$ have specified meanings. The products are useful as 5-HT$_{1A}$ antagonists.

Novel diesters of formula D useful as intermediates in the process are also disclosed.

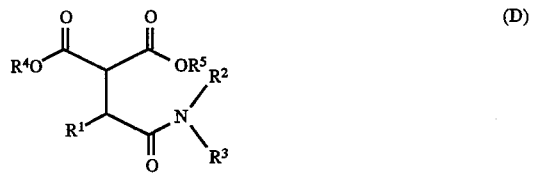

7 Claims, No Drawings

PROCESS FOR PREPARING OPTICALLY ACTIVE AMIDE DERIVATIVES

This is a 35 USC 371 National Stage application of International application PCT/GB93/0290 filed Oct. 8, 1993.

This invention relates to a novel asymmetric synthesis for preparing amide derivatives and to intermediates useful in the synthesis.

The invention particularly relates to a process for preparing optically active amides of the general formula

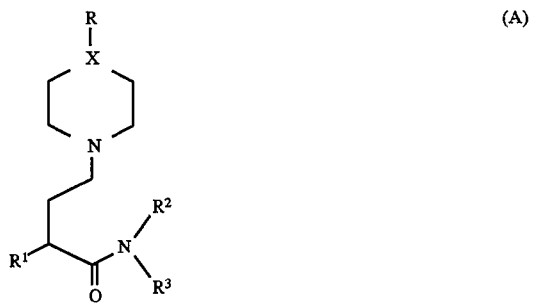

and the pharmaceutically acceptable salts thereof.

In formula A,

X represents

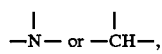

R represents a mono or bicyclic aryl or heteroaryl group, $R^1$ is an aryl or heteroaryl radical, $R^2$ is hydrogen or lower alkyl, $R^3$ is hydrogen, an alkyl group of 1 to 10 carbon atoms, cycloalkyl of 3 to 12 carbon atoms, cycloalkyl-(lower) alkyl, aryl or aryl(lower)alkyl or $R^2$ and $R^3$ together with the nitrogen atom to which they are both attached represent a saturated heterocyclic ring which may contain a further hetero atom [eg an azetidino, pyrrolidino, piperidino, hexahydroazepino, heptamethyleneimino, morpholino or piperazino ring which may be optionally substituted by, for example, lower alkyl, aryl, aryl(lower)alkyl, lower alkoxy, halogen or halo(lower)alkyl].

The term "lower" as used herein means that the radical referred to contains 1 to 6 carbon atoms. Preferably such radicals contain 1 to 4 carbon atoms. Examples of "lower alkyl" radicals are methyl, ethyl, propyl, isopropyl, butyl, tert.-butyl, pentyl and isopentyl. When $R^3$ is an alkyl group a particularly preferred radical is a tertiary alkyl radical such as tert.butyl.

A cycloalkyl group can contain 3 to 12 carbon atoms. Preferably a cycloalkyl group is cyclopentyl, cyclohexyl or cycloheptyl, most preferably cyclohexyl. Cycloalkyl groups also include bicyclic, tricyclic and tetracyclic groups, eg adamantyl.

When used herein "aryl" means an aromatic radical having 6 to 12 carbon atoms (eg phenyl or naphthyl) which optionally may be substituted by one or more substituents commonly used in medical chemistry, eg substituents such as lower alkyl, lower alkoxy (eg methoxy, ethoxy, propoxy, butoxy), loweralkylthio, halogen, halo(lower)alkyl (eg trifluoromethyl), nitro, cyano, carboxamido, (lower) alkoxycarbonyl, amino, (lower)alkylamino or di(lower) alkylamino substituents. Two substituents on the aromatic ring may be connected together to form another ring system.

For example R may be a bicyclic oxygen-containing radical such as a optionally substituted radical of the formula

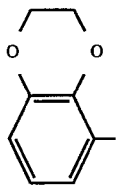

The term "heteroaryl" refers to an aromatic radical containing one or more hetero atoms (eg oxygen, nitrogen, sulphur) and which may be optionally substituted by one or more substituents. Some examples of suitable substituents are given above in connection with "aryl" radicals. The heteroaryl radical may, for example, contain up to 10 ring atoms; for example the heteroaryl radical may be a monocyclic radical containing 5 to 7 ring atoms. Preferably the hetero ring contains a nitrogen hetero atom with or without one or more further hetero atoms.

When R is a heteroaryl radical it is preferably an optionally substituted pyrimidyl (particularly 2-pyrimidyl), quinolinyl or indolyl [particularly indol-4-yl which may be optionally substituted eg by (lower)alkoxycarbonyl] radical.

When $R^1$ is a heteroaryl or heteroaryl-lower alkyl the "heteroaryl" group is preferably a nitrogen containing heteroaryl radical (eg an optionally substituted pyridinyl, pyrimidinyl or pyrazinyl radical) or a heteroaryl radical containing an oxygen or sulphur atom as a hetero atom eg an optionally substituted thienyl or furyl group.

Preferred compounds of formula A have the following characteristics either singly or in any possible combination:

(a) X is

(b) R is optionally substituted phenyl, eg o-alkoxy-phenyl (particularly o-methoxyphenyl)

(c) $R^1$ is phenyl (d) $R^2$ and $R^3$ together with the nitrogen atom to which they are both attached represent a saturated heterocyclic ring, particularly hexahydroazepino.

Compounds of formula (A) are useful because of their pharmacological activity, eg as 5-$HT_{1A}$-antagonists. The compounds and their uses are disclosed, for example, in GB 2230780 A, GB 2290781 A, GB 2248836 A, GB 2254324 A, GB 2262093 A and WO-GB 93/01542. The prior specifications refer to the preparation of enantiomers by, for example, resolution of the racemates. The process of the present invention avoids the inconvenient resolution step.

The invention particularly relates to a process for preparing (−)-(R)-2,3,4,5,6,7-hexahydro- -1-[4-[4-(2-methoxyphenyl)piperazin-1-yl]-2-phenyl]-butanoyl-1H-azepine and the pharmaceutically acceptable acid addition salts thereof. The compound, in its free base form, has the formula

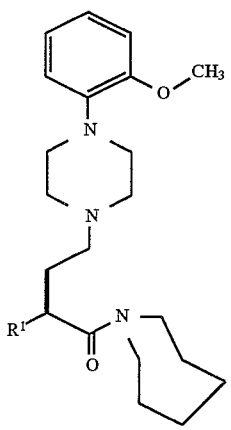

The compound and its use as a 5-HT$_{1A}$-antagonist is disclosed in GB-A-2248836. Example 2(a) of GB-A-2248836 describes the preparation of the compound and its salts by resolution of a corresponding racemate.

It has now been found that compound (I) can be prepared in good yield by an asymmetric synthesis from readily available starting materials thus avoiding an inconvenient resolution step.

An essential step in the synthesis of the present invention which forms the first aspect of the present invention, is a process which comprises condensation of an aldehyde of formula

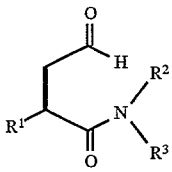
(B)

(where R$^1$ R$^2$ and R$^3$ are as defined above) with an amine of formula

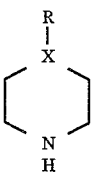
(C)

(where X and R are as defined above) to give the compound of formula (A). For example an aldehyde of formula

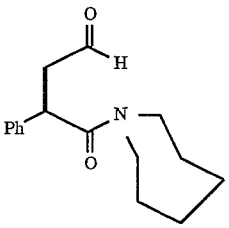
(II)

may be condensed with a piperazine derivative of formula

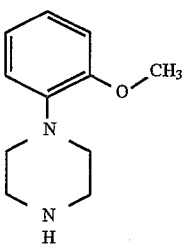
(III)

to give the compound of formula (I). We have found that the stereochemisty of the aldehyde is retained during the condensation to give the desired enantiomeric form of the product in good yield. In contrast if for example the piperizine (III) is condensed with an entantiomeric form of an alkylating agent of formula

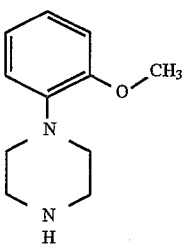

where X is halogen, racemisation occurs during the reaction.

The condensation of the aldehyde of formula (B) with the piperazine of formula (C) may be carried out, for example, in presence of a reducing agent such as sodium triacetoxyborohydride or sodium cyanoborohydride.

The aldehyde of formula (B) may be prepared by a process which comprises hydrolysing a diester of formula

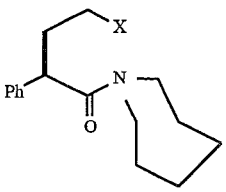
(D)

(where R$^1$ R$^2$ and R$^3$ are as defined above and R$^4$ and R$^5$ are each lower alkyl groups of 3 to 6 carbon atoms) to give a diacid amide of formula

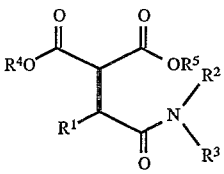
(E)

(where R$^1$ R$^2$ and R$^3$ are as defined above) decarboxylating the diacid amide of formula (E) to give the monoacid amide of formula

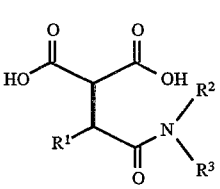
(F)

(where R$^1$ R$^2$ and R$^3$ are as defined above) and reducing the monacid amide of formula (F) to the aldehyde of formula (B).

Preferably $R^4$ and $R^5$ are both branched chain alkyl groups such as isopropyl or, more preferably, tertiary butyl.

The hydrolysis of the diester can be effected with an acid, e.g. formic acid, trifluoroacetic acid.

The diacid amide need not be isolated before carrying out the decarboxylation process. The decarboxylation may be carried out by heating the diacid amide in an inert solvent, e.g. acetonitrile, optionally in presence of a catalytic amount of $Cu_2O$.

The monacid amide (F) may be reduced directly to the aldehyde (B) with, for example, an aminoalane, but it is prefered to reduce the monoacid amide to the alcohol of formula

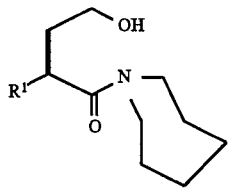
(G)

and then oxidise the alcohol (G) to the aldehyde (B). The reduction to the alcohol may be effected by using a reducing agent that does not reduce the amide group, e.g. reduction with $Me_2S.BH_3$, preferably in the presence of $BF_3.Et_2O$, or alternatively activation of the monoacid amide by reaction with bis-succinimido carbonate followed by reduction with $NaBH_4$. The oxidation of the alcohol (G) to the aldehyde (B) may be effected with, for example, tetra-n-propylammonium per-ruthenate, DMSO, oxalyl chloride triethylamine.

The diesters of formula (D) are novel compounds provided by the invention. Particularly preferred are the diesters of formula

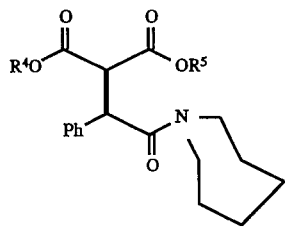
(IV)

(where $R^4$ and $R^5$ are as defined above). These are used as intermediates for the compound of formula (I).

The diesters of formula (D) may be prepared by a novel process which comprises reacting an activated α-hydroxy amide of formula

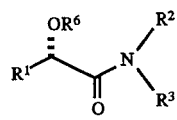
(H)

(where $R^1$, $R^2$ and $R^3$ are as defined above and $R^6$ is an activating group which maintains chirality such as an arylsuphonyl group, e.g. p-toluenesulphonyl) with a dialkylmalonate of formula

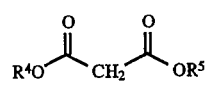
(J)

where $R^4$ and $R^5$ are as defined above. The dialkylmalonate is preferably reacted in the form of its sodium or potassium salt. It has been found that the reaction is stereospecific with inversion of the centre at the benzylic position to give the desired stereochemistry in the diester (D). The stereospecificity of the process is surprising since the compound of formula (H) has an aryl or heteroaryl group and an amide GROUP which would be expected to produce a much more acidic proton (in the benzylic position) than the corresponding proton in the prior art compound in which equivalent groups are respectively alkyl and ester (M. Larcheveque et al. Synthesis, February 1991, 162–164). The more labile proton would have been expected to give rise to a racemic product.

The activated α-hydroxy amides of formula (H) can be prepared from the S-(+)-mandelic acid derivatives of formula

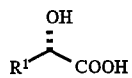

(where $R^1$ is as defined above) for example the hydroxy groups of S-(+)-mandelic acid of formula

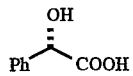
(V)

may be protected to give a protected derivative of formula

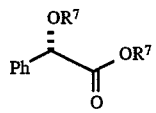
(VI)

(where $R^7$ is a protecting group such than $OR^7$ is stable when —COOR is converted to —COhalogen). halogenating the protected derivative (VI) to give an acyl halide of formula (VII)

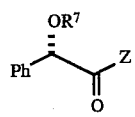
(VII)

(where $R^7$ is as defined above and Z is chlorine or bromine), reacting the acyl halide (VII) with an amine of formula $NHR^2R^3$ (where $R^2$ and $R^3$ are as defined in claim 1) to give the protected hydroxy amide

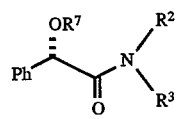
(VIII)

(where $R^2$ $R^3$ and $R^7$ are as defined above) removing the protecting group from the protected hydroxy amide (VIII) to give the hydroxy amide (IX)

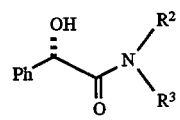
(IX)

(where $R^2$, and $R^3$ are as defined above), and activating the hydroxy amide (IX) to give the α-activated hydroxy amide (H).

The prefered protecting groups, $R^7$ for S-(+)-mandelic acid are trimethysilyl or tertbutyldimethylsilyl. The mandelic acid may, for example, be reacted with 1,3-bis (trimethylsilyl)urea or with tert.butyldimethylsilyl chloride.

The protected derivative (VI) may be halogenated with, for example, oxalyl chloride to give an acyl halide (VII) where Z is chlorine or, more preferably with triphenyl phosphine/bromine to give an acyl halide (VII) where Z is bromine. The acyl halide (VII) need not be isolated before reaction with the amine (eg hexamethyleneimine).

The protecting group $R^7$ may be removed from the protected hydroxy amide (VIII) with an acid e.g. citric acid.

The hydroxyamide (VIII) may be activated with a reagent that does not destroy the chirality of the compound. Suitable reagents include arylsulphonic anhydrides (e.g. p-toluenesulphonic anhydride) and methanesulphonic anhydride.

The processes desribed above may be carried out to give a product in the form of a free base or as an acid addition salt. If the product is obtained as an acid addition salt, the free base can be obtained by basifying a solution of the acid addition salt. Conversely, if the product of the process is a free base an acid addition salt, particularly a pharmaceutically acceptable acid addition salt, may be obtained by dissolving the free base in a suitable organic solvent and treating the solution with an acid, in accordance with conventional procedures for preparing acid addition salts from base compounds.

Examples of acid addition salts are those formed from inorganic and organic acids, such as sulphuric, hydrochloric, hydrobromic, phosphoric, tartaric, fumaric, maleic, citric, acetic, formic, methanesulphonic, p-toluenesulphonic, oxalic and succinic acids.

The following examples illustrate the invention.

EXAMPLE 1

(S)-Bis(trimethylsilyl)mandelic acid

To a solution of (S)-(+)-mandelic acid (62.49 g, 0.41 mol) in dry dichloromethane (250 ml) was added 1,3-bis (trimethylsilyl)urea (88.40 g, 0.41 mol). The reaction mixture was stirred for twenty four hours at room temperature under argon. The suspension was refluxed for twelve hours.

The suspension was allowed to cool. Celite was added and the suspended urea removed by suction through a bed of Celite. The dichloromethane solution was filtered directly into the suspension of triphenyl phosphine dibromide prepared in Example 2.

EXAMPLE 2

(S)-2,3,4,5,6,7-Hexahydro-1-(2-trimethylsilyloxy-2-phenyl )ethanoyl-1H-azepine

To a stirred, ice cooled solution of triphenyl phosphine (107.54 g, 0.41 mol) in dry dichloromethane (400 ml) was added dropwise bromine (21.1 ml, 0.41 ml) under argon. Following the addition the cooling bath was removed and the reaction mixture obtained in Example 1 filtered directly into the freshly prepared triphenyl phosphine dibromide suspension.

The reaction mixture was stirred under argon at room temperature until it became homogeneous. The cooling bath was returned and hexamethyleneimine (143 ml, 1.27 mol) added dropwise over forty five minutes. Following addition the cooling bath was removed and the reaction mixture allowed to attain room temperature.

After a further hour the solvent was removed and the solid extracted with hexane (2×1.5l). This was filtered by suction through Celite. The solvent was removed and the residue distilled under vacuum.

At 0.5 m bar:

125°–155° C. discarded

155°–165° C. main fraction (86.77 g, 69%)

EXAMPLE 3

(S)-2,3,4,5,6,7-Hexahydro-1-(2-hydroxy-2-phenyl) ethanoyl-1H-azepine

The OTMS ether obtained in Example 2 (86.77 g, 0.284 mol) was dissolved in methanol (200 ml) and catalytic citric acid added. The solvent was removed and the residue dissolved in dichloromethane. This was washed with sodium bicarbonate, saturated sodium chloride solution, dried (MgSO4)and reduced under vacuum. The colourless oil was distilled under vacuum.

At 0.35m bar: 134°–138° C. (62.9 g,95%)

EXAMPLE 4

(S)-2,3,4,5,6,7-Hexahydro-1-(2-p-toluenesulphonyloxy-2-phenyl)ethanoyl-1H-azepine The α-hydroxy amide from Example 3 (34.88 g, 150 mmol) was stirred in dry dichloromethane (250 ml) under argon. To this solution was added p-toluenesulphonic anhydride (50.31 g, 150 mmol). Pyridine (12.1 ml, 156 mmol) was added over one hour. The reaction mixture was stirred for eighteen hours room temperature.

The dichloromethane solution was washed with cold HCl (1N), saturated sodium chloride solution and dried (MgSO$_4$). Removal of the solvent gave a solid which was recrystallised from acetone. The supernatant was taken to dryness and recrystallised from acetone/hexane. A combined mass of 47.0 g (81%) was obtained.

EXAMPLE 5

(R)-2,3,4,5,6,7-hexhydro-1-(3-di-tert-butylcarboxylate-2-phenyl)propanoyl-1H-azepine To a stirred solution of di-tert-butyl malonate C9.53 ml, 45.6 mmol) in dry N,N-dimethylformamide under argon was added sodium hydride (1.21 g, 40.3 mmol, 80% suspension in oil) in two portions over a period of ninety minutes. After complete reaction of the sodium hydride had taken place the solution was warmed to 80° C. and the tosylate from Example 4 (15.0 g, 38.7 mmol) added immediately as a hot solution in dry N,N-dimethyformamide (20 ml).

The reaction was stirred at this temperature for a further two hours. The solution was allowed to cool to room temperature. Water was added followed by hexane. The hexane was removed and the aqueous layer extracted with two further portions of hexane. The organic layers were combined, washed with saturated sodium chloride solution, dried (MgSO$_4$) and reduced under vacuum.

The solid residue was recrystallised from hexane to afford 5.93 g. The supernatant was purified by pressure silica gel column chromatography eluting with hexane/diethyl ether (2/1) to give after recrystallisation a further 3.3 g. A total of 9.23 g (55%) was thus obtained.

EXAMPLE 6

(R)-2,3,4,5,6,7-Hexahydro-1-(3-carboxy-2-phenyl) propanoyl-1H-azepine

The di-tert-butyl ester from Example 5 (9.64 g, 22.3 mmol) was added to formic acid (75 ml) cooled to 0° C. with stirring. The cooling bath was removed and stirring continued for three hours. The solvent was removed under reduced pressure (bath temperature less than 40° C.). Dichloromethane was used to co-evaporate the formic acid and a stable white foam was obtained.

The foam was dissolved in dry acetonitrile and refluxed under argon for three hours. The solution was allowed to cool overnight.

The solvent was removed and the oily residue taken up in dichloromethane. The acid was removed by extraction with sodium hydroxide (10%) (20 ml) The aqueous layer was washed with ether and then taken to pH6 by the careful addition of cold HCl (1N). The mono-acid was extracted with ether, washed with saturated sodium chloride solution, dried (MgSO$_4$)and reduced under vacuum to a colourless oil (4.95 g, 81%).

EXAMPLE 7

(R)-2,3,4,5,6,7-Hexahydro-1-(4-hydroxy-2-phenyl) butanoyl-1H-azepine

To a solution of the acid from Example 6 (approx. 80% chemically pure, >95% (R) (315 mg, 1.15 mmol) in dry THF at room temperature under argon was added BF$_3$.Et$_2$O(183 µl, 1.5 mmol). The solution was stirred for ten minutes before adding Me$_2$S.BH$_3$ in THF (2M) (744 ml, 15 mmol). The reaction mixture was stirred at room temperature for four hours. Water was added cautiously and the volatiles removed.

The residue was partitioned between ether and saturated sodium bicarbonate solution. The ether layer was further washed with saturated sodium chloride solution and dried (MgSo$_4$). Removal of the solvent following filtration gave the alcohol (200 mg, 67%).

EXAMPLE 8

(R)-2,3,4,5,6,7-Hexahydro-1-(3-carboxaldehyde-2-phenyl)propanoyl-1H-azepine

The alcohol from Example 7 (226 mg, 0.86 mmol) was dissolved in dry dichloromethane (8 ml) at room temperature under argon, N-methylmorpholine N-oxide (152 mg, 1.29 mmol) and 4 Å-molecular sieves added with stirring. After ten minutes tetra-n-propylammonium per-ruthenate 15 mg, 0.043 mmol) was added.

Stirring was continued for four hours. The reaction was diluted with dichloromethane (30 ml) and washed successively with saturated sodium sulphite solution (10 ml) saturated sodium chloride solution (10 ml) and saturated copper (II) sulphate (10 ml). The organic layer was dried (MgSO$_4$), filtered and used without further purification in Example 9.

EXAMPLE 9

(−)-R-2,3,4,5,6,7-Hexahydro-1-[4-[4-(2-methoxyphenyl)-piperazin-1-yl]-2-phenyl]butanoyl-1H-azepine To the solution of aldehyde produced in Example 8 maintained at room temperature under argon was added 1-(2-methoxyphenyl)piperazine (165 mg, 0.86 mmol) and sodium triacetoxyborohydride (182 mg, 0.86 mmol) followed by acetic acid (98 µl, 1.72 mmol).

The reaction mixture was stirred for three hours. The reaction mixture was washed with saturated sodium bicarbonate (10 ml), saturated sodium chloride solution (10 ml), dried (MgSO$_4$), and reduced in vacuo. The resulting oil was purified by flash chromatrography eluting with dichloromethane/methanol (20/1) to give the title compound.

The material was shown to be identical to an authentic sample by $^1$H, $^{13}$C NMR, IR and chiral stationary phase HPLC.

I claim:

1. A process for preparing an optically active amide of formula

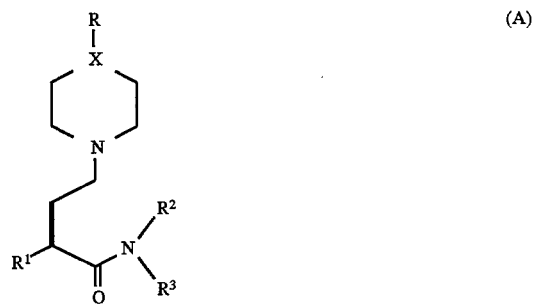

(A)

or a pharmaceutically acceptable salt thereof where

X represents

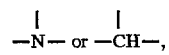

—N— or —CH—,

R represents a mono or bicyclic aryl or heteroaryl group,

R$^1$ is an aryl or heteroaryl radical,

R$^2$ is hydrogen or lower alkyl,

R$^3$ is hydrogen, an alkyl group of 1 to 10 carbon atoms, cycloalkyl of 3 to 12 carbon atoms, cycloalkyl-(lower) alkyl, aryl or aryl(lower)alkyl or R$^2$ and R$^3$ together with the nitrogen atom to which they are both attached represent a saturated heterocyclic ring which may contain a further hereto atom which process comprises condensing an aldehyde of formula

(B)

(where R$^1$ R$^2$ and R$^3$ are as defined above) with an amine of formula

(C)

(where X and R are as defined above).

2. A process of claim 1 in which X is —N—, R is o-methoxyphenyl, R$^1$ is phenyl and R$^2$ and R$^3$ together with the nitrogen atoms to which they are both attached represent hexahydroazepino.

3. A process for producing an optically active aldehyde of formula (B)

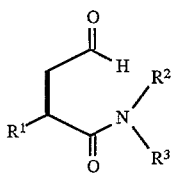

or a salt thereof, where

R¹ is an aryl or heteroaryl radical,

R² is hydrogen or lower alkyl,

R³ is hydrogen, an alkyl group of 1 to 10 carbon atoms, cycloalkyl of 3 to 12 carbon atoms, cycloalkyl(lower)alkyl, aryl or aryl(lower)alkyl or R² and R³ together with the nitrogen atom to which they are both attached represent a saturated heterocyclic ring which may contain a further hetero atom which process comprises (A) hydrolyzing a diester of formula (D)

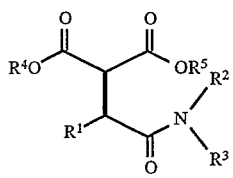

where R¹, R² and R³ are as defined above and R⁴ and R⁵ are each lower alkyl groups of 3 to 6 carbon atoms, to give a diacid amide of formula (E)

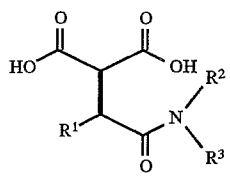

where R¹, R² and R³ are as defined above, (B) decarboxylating the diacid amide of formula (E) to give the monoacid amide of formula (F)

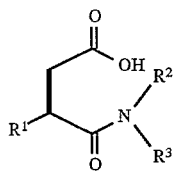

(where R¹, R² and R³ are as defined above), and (C) reducing the monoacid amide of formula (F) to the aldehyde of formula (B).

4. A process for preparing a diester of formula (D)

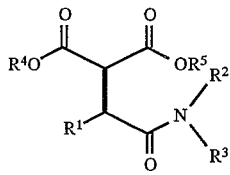

(where R¹, R² and R³ are as defined in claim 1 and R⁴ and R⁵ are each lower alkyl groups of 3 to 6 carbon atoms) which comprises reacting an activated α-hydroxy amide of formula

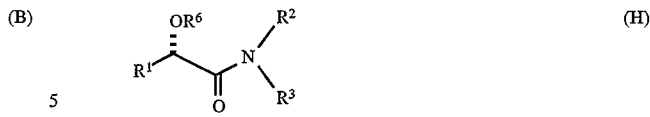

(where R¹, R² and R³ as defined in claim 1 and R⁶ is an activating group which maintains chirality) with a dialkylmalonate of formula

(where R⁴ and R⁵ are as defined above).

5. A process according to claim 3 in which the activated α-hydroxy amide of formula (H) where R¹ is phenyl is prepared by protecting the hydroxy groups of S-(+)-mandelic acid of formula

to give a protected derivative of formula

(where R⁷ is a protecting group), halogenating the protected derivative (VI) to give an acyl halide of formula (VII)

(where R is as defined above and Z is chlorine or bromine), reacting the acyl halide (VII) with an amine of formula

(where R² and R³ are as defined in claim 1) to give a protected hydroxy amide of formula

(where R², R³ and R⁷ are as defined above), removing the protecting group from the protected hydroxy amide (VIII) to give the hydroxy amide (IX)

(where R² and R³ are as defined above) and activating the hydroxy amide (IX) to give the α-activated hydroxy amide of formula (H).

6. A diester of formula (D)

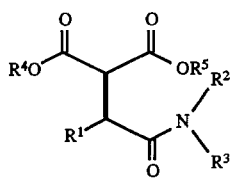

(D)

or a pharmaceutically acceptable salt thereof, where
- $R^1$ is an aryl or heteroaryl radical,
- $R^2$ is hydrogen or lower alkyl,
- $R^3$ is hydrogen, an alkyl group of 1 to 10 carbon atoms, cycloalkyl of 3 to 12 carbon atoms, cycloalkyl(lower)alkyl, aryl or aryl(lower)alkyl, or
- $R^2$ and $R^3$ together with the nitrogen atom to which they are both attached represent a saturated heterocyclic ring which may contain a further hetero atom; and $R^4$ and $R^5$ are each lower alkyl groups of 3 to 6 carbon atoms.

7. A diester as claimed in claim 6 of formula

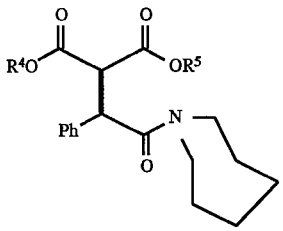

(IV)

where $R^4$ and $R^5$ are as defined in claim 6.

* * * * *